(12) United States Patent
Gray

(10) Patent No.: US 6,449,896 B1
(45) Date of Patent: Sep. 17, 2002

(54) CROP WEIGHING

(76) Inventor: David Gray, Moyra, Falcarragh, County Donegal (IE)

( * ) Notice: Subject to any disclaimer, the term of this patent is extended or adjusted under 35 U.S.C. 154(b) by 0 days.

(21) Appl. No.: 09/643,748

(22) Filed: Aug. 23, 2000

(30) Foreign Application Priority Data

Aug. 23, 1999 (IE) ................................................ S990718

(51) Int. Cl.⁷ .................................................. A01G 9/00
(52) U.S. Cl. ............................ 47/17; 119/416; 119/417; 119/418; 119/419; 119/420; 119/421
(58) Field of Search ................................ 119/416, 417, 119/418, 419, 420, 421; 47/17

(56) References Cited

U.S. PATENT DOCUMENTS

| | | | | |
|---|---|---|---|---|
| 3,063,195 A | * | 11/1962 | Ravich | 47/17 |
| 3,398,481 A | * | 8/1968 | Lake | 47/17 |
| 4,339,074 A | * | 7/1982 | Nissmo et al. | 236/47 |
| 4,430,828 A | * | 2/1984 | Oglevee et al. | 165/205 |
| 4,569,150 A | * | 2/1986 | Carlson et al. | 47/17 |
| 5,163,380 A | * | 11/1992 | Duffy et al. | 119/418 |

* cited by examiner

*Primary Examiner*—Charles T. Jordan
*Assistant Examiner*—Stephen A. Holzen
(74) *Attorney, Agent, or Firm*—Jacobson Holman, PLLC

(57) ABSTRACT

A method of determining the weight of animals and the development of plants in a controlled environment. The method includes measuring the increase in $CO_2$ production over a test period. $CO_2$ production is a measure of the metabolic rate and this is related to weight of animals and development of crops which can often be determined by weight. There is illustrated a poultry rearing house having vents, lights and an air heater. $CO_2$ sensors are connected to a $CO_2$ controller and in turn to a central controller. To test the increase in $CO_2$ production over time, the birds are settled into a passive state with no feed and the lights turned off. The level of $CO_2$ produced is measured. The vents are closed. After a time, the rate of $Co_2$ produced is measured and the increase calculated.

11 Claims, 7 Drawing Sheets

CROP WEIGHING

BACKGROUND OF THE INVENTION

1. Field of the Invention

The present invention relates to a method of and apparatus for determining the body weight of animals and the development of plants housed in a controlled environment within an enclosure, 2. Background Information In the rearing of animals such as pigs and poultry it is known to rear the animal in an enclosure with a tightly controlled environment. Indeed many types of food are also produced in these enclosed environments. Usually the animals reared are of a uniform genetic type. In rearing such animals the producer is attempting to optimise the food conversion ratios minimise energy arid other overhead costs and effectively to determine the optimum time for removing all or some of the animals for subsequent processing. The elements of successful production is the control of the environment and all the other conditions prevailing.

Plants are grown in substantially the same way and thus it is not uncommon for people engaged in intensive animal rearing to refer to them as crops. Thus in this specification the term crop is used to encompass animals and plants. While the invention described herein is particularly relevant for the determining of the body weight of animals housed in a controlled environment within an enclosure, the method and apparatus is equally well adapted to the determination of the body weight or more strictly the development of plants since in many cases the development or maturity for harvesting of a plant is not determined by its weight and thus the general terms "crop" and "development" are used.

An example of animal rearing is in the production of poultry. The birds, which are usually of a uniform genetic type in that they are generally bred from a common grandparent stock thus start off as almost totally uniform animals. The producers then try to provide the optimum environmental conditions for effective growth and general welfare. The producer has a maior problem in that the producer wants to have the optimum average bird weight when the poultry is about to be slaughtered so that the best price can be obtained. Since in moat cases the price paid is based on average bird weight it is essential to know exactly what the weight is. Further because buyers such as supermarket chains tend to pay a fixed price based on minimum bird weight the need to be able to ascertain the average bird weight is all important.

Feed forms the single largest factor in the cost of production being of the order of 60% of the total overall cost and thus optimising the feed conversion ratio is the single most important factor in the financial health of the operation. Thus knowing the correct time to remove the animals for further processing, often referred to as harvesting, is vital and this is when the bulk of the crop has met the target weight criteria. This is irrespective of the target weight criteria.

In poultry production a number of methods are used to determine the weights. The first method is a simple manual sampling method in that workers move through the birds with weighing scales and sample the crops by hand. This method produces a relatively accurate assessment of the average bird weight. However, it is labor intensive and thus costly to collect the information manually and then correlate the collected data into an electronic data base.

The second method is to provide electronic weighing platforms at various points throughout the production area. These platforms take weight measurements as birds climb on and off them. While this method is more suitable for automatic electronic capture analysis on data transmission it suffers from the disadvantage that is dependent on animal behaviour. Unfortunately the same animals tend to mount the weighing platform over and over again so that accurate sampling cannot be guaranteed. Further the actual weighing scales or platforms are relatively expensive and a significant number of platforms are required so that the total cost of this method is also high.

Objects

The present invention is directed towards providing an improved method and apparatus for determining the development of plants and the average body weight or average gross body weight more correctly of a number of animals housed in an enclosure within a controlled environment.

SUMMARY OF THE INVENTION

According to the invention, there is provided a method of determining the development of a crop housed in a controlled environment within an enclosure including the acts of analysing and measuring the gas constituents of the environment before and after a preset time to determine the change in the concentration of one or more gases during a test period to estimate the metabolic rate of the animals and hence their weight.

Preferably, the increase in the quantity of carbon dioxide or the decline in the quantity of oxygen is measured. It has been found that depending on the metabolic activity of the animals, the $CO_2$ gas emission varies with body weight for animals and with plant development generally. $CO_2$ and $O_2$ are good control gases. It will be appreciated that this is a much more efficient and dynamic way of measuring crop development than methods used heretofore, such as, for example, sample weighing.

Ideally, the enclosure is sealed during the test period and preferably the air is recirculated within the enclosure during the test period.

It is also advantageous to cause the environment within the enclosure to assume a rest phase with minimal crop activity. In this way, no extraneous factors are impinged on the test results. Since rest periods occur naturally during certain times of rearing, particularly night time which is largely for staff convenience, this is a time within which the test may be conveniently carried out. It is envisaged that the metabolic rate of the crop will need to be compared to the actual weight for animals or some other assessment criterion for plants to calibrate the measurements. It is also envisaged that prior to final removal of the crop from the enclosure, the metabolic rate of the crop is taken and the development estimated and on removal and further processing, the development is measured to provide more accurate correlation of metabolic rate with development for future control.

It is envisaged that with the present invention, the gas constituents in the air being removed from the endosure are measured to enable the control of the air input for optimal environmental conditions. In this way, further control of the growing environment may be provided. It is also envisaged that the control of the development of the crop, whether it be the growth of poultry or the development of plants, may be accurately controlled so that when it is known that there will be periods of greater demand, the crop can be developed quickly to achieve the right weight and development at the target time. Alternatively, when it is known that there is a drop in demand, than the general development can be slowed down. This can be done by:

dividing the expected crop rearing time into a plurality of control periods;

determining the development of the crop at the end of each control period; and varying the growing conditions for the next control period to take account of the previously recorded development to obtain a desired development gain for the next control period.

In this latter method, to determine the optimum growing conditions including environmental conditions and food quantities and type to obtain the desired development gain, the steps are performed of carrying out a number of tests on separate samples of crops for each control period comprising:

varying the environmental conditions and food quantities and types for the control periods to provide a rearing condition;

obtaining the crop development for each control period and rearing conditions; and recording the rearing conditions and development gain for each control period to provide the optimum growing conditions for a specific control period having regard to initial each development at the start of the control period and desired crop development at the end of the period.

It is also envisaged that the methods according to the present invention will allow more accurate determination of optimum growing conditions. In addition to measuring the gas constituents of the environment for weight and other measurement, the gas constituents are measured during the growing period and the measurements used to control the air intake into the environment for optimum growing conditions.

Further, the invention provides a crop roaring house of the type comprising an enclosed room and means for controlling the environment including at least controllable air vents and healing means in which there is provided a gas sensor for determining the concentration of selected gases in the environment. Ideally, the gas sensor includes $CO_2$ and/or $O_2$ sensing means.

Ideally, there is an air recirculation fan and the gas sensor is mounted in the path of the air flow of the fan.

In one embodiment of the invention, the crop rearing house includes a monitoring unit comprising:

an airtight enclosure;

a plurality of air monitoring sensors;

an inlet for ambient air;

an inlet for rearing house air;

fans to control the intake of air into the unit; and control means to regulate the operation of the fans and sensors.

BRIEF DESCRIPTION OF THE DRAWINGS

The invention will be more clearly understood from the following description of some embodiments thereof, given by way of example only, with reference to the accompanying drawings, in which.

DESCRIPTION OF THE PREFERRED EMBODIMENTS

Figure 1:
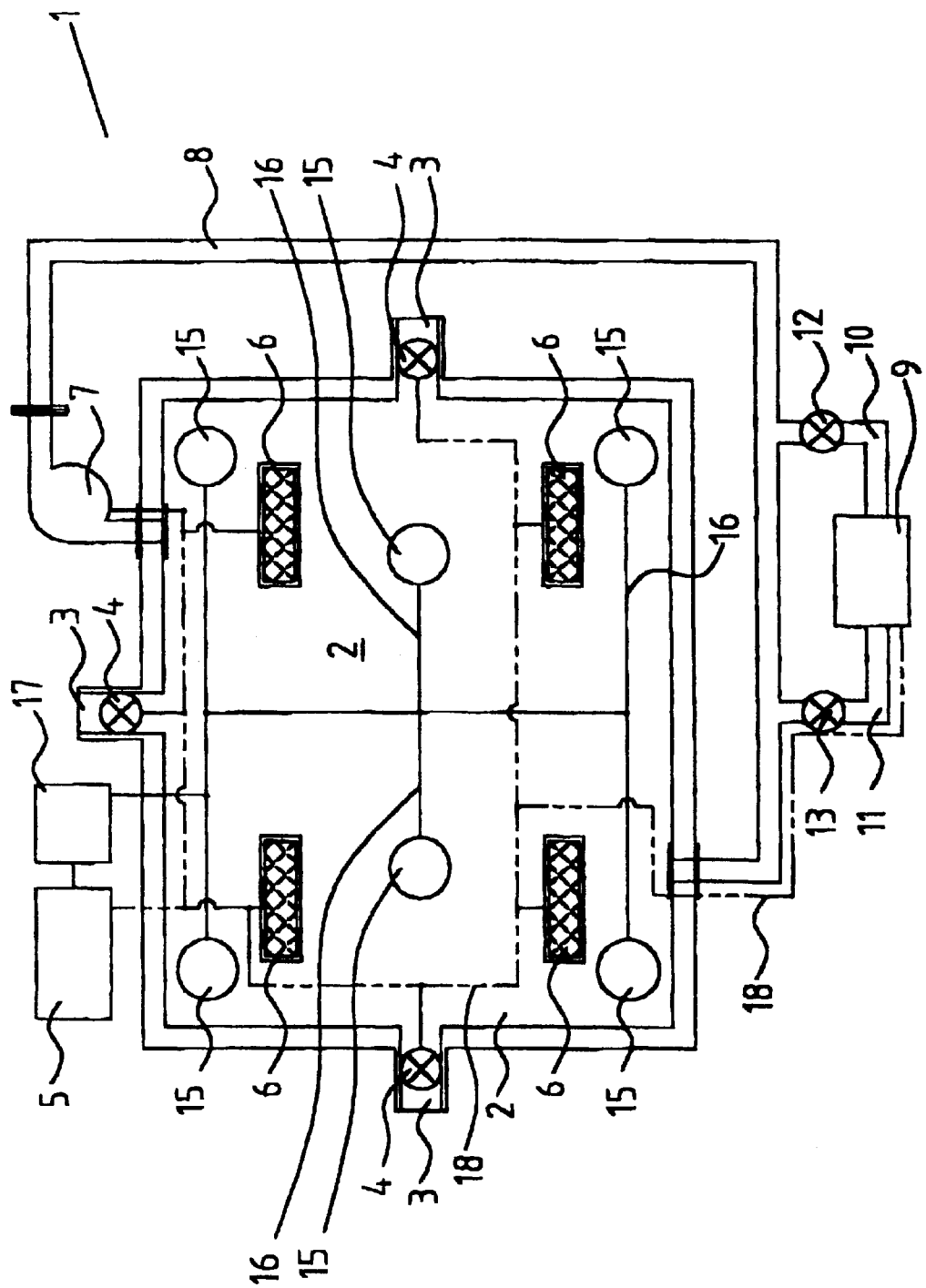
FIG. 1 is a typical layout of a poultry rearing house according to the invention.

Referring to the drawings and initially to FIG. 1, there is provided a crop rearing house indicated generally by the reference numeral 1 comprising an enclosure or enclosed room 2 having air vents 3 which incorporate valves 4 connected to a central controller 5, as are also lights 6. The crop rearing house 1 is for poultry. A recirculation fan 7 and air duct 11 are also provided. An air heater 9 having an air intake duct 10 and an air outlet duct 11, each connected to the air duct 8 and housing valves 12 and 13 respectively, is also provided. Both the air circulation fan 7 and the air heater 9 are connected to the central controller 5. A plurality of $CO_2$ sensors 15 are mounted in the room 2 and are connected by wires 16 to a $CO_2$ controller 17 connected to the central controller 5. Other wires 18 are illustrated by interrupted lines.

Figure 2:
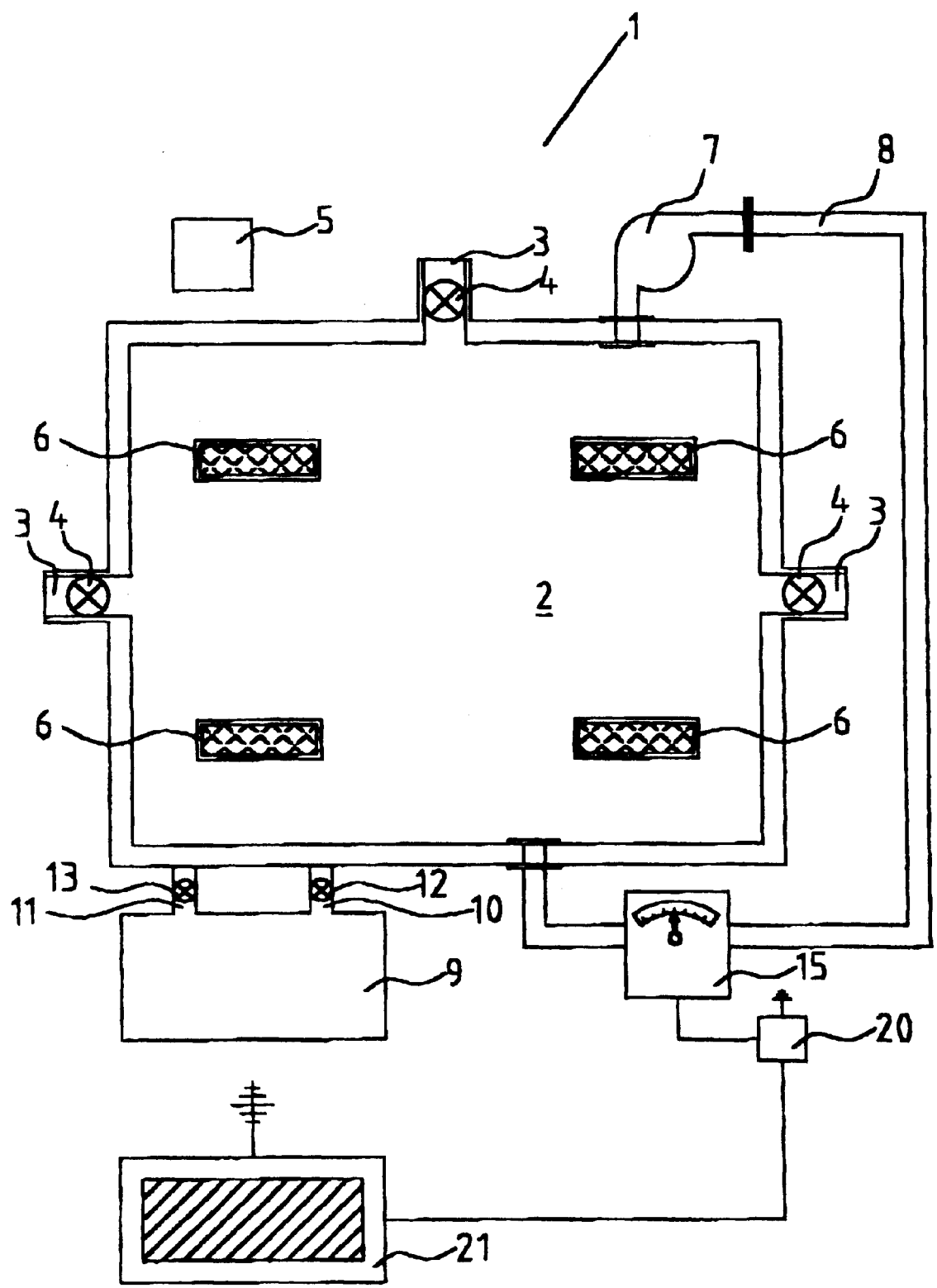
FIG. 2 is a layout of an alternative construction of poultry rearing house.

Referring now to FIG. 2, there is illustrated an alternative construction of crop rearing house, again identified by the reference numeral 1 and parts similar to those described with reference to the previous drawings are identified by the same reference numerals. In this embodiment, there is only one $CO_2$ sensor 15 mounted in the air duct while a separate heater 9 is provided. In this embodiment, the $CO_2$, controller 17 is incorporated in the $CO_2$ sensor 15 and together with the central controller 5 is connected to a radio transmitter 20 which in turn communicates to an externally located master control receiver 21 which incorporates computers, etc. to allow the downloading of information from both the central controller 5 and the $CO_2$ sensor 15.

Essentially, the same method of carrying out the invention is provided irrespective of whether the crop rearing house of FIG. 1 or 2 is used. Such a crop rearing house would be used, for example, for poultry rearing which would have the ventilation and heating system to provide an enclosed controlled environment. The following steps are then carried out.

1. All lights 6 and other equipment are turned off. This settles the birds and activity becomes uniform and minimal. This is generally know as a rest period and correlates to the rest periods normally encountered by the birds.
2. The enclosure, namely, the crop rearing house 1 is sealed cutting off outside air exchange by closing the air vents 3 and thus no further air is delivered into or out of the enclosure.
3. The air recirculation fan 7 is turned on to make the internal air distribution uniform. Additional air mixer fans, not shown, may also be operated.
4. A measurement of $CO_2$ gas concentration by the $CO_2$ sensors 15 is carried out immediately after the sealing takes place and is recorded in the $CO_2$ controller 17.
5. A fixed time pefiod is selected.
6. A second measurement of $CO_2$ gas concentration is made and again recorded.
7. Normal ventilation is resumed.
8. The calculation of total bird weight is made by comparison with the increase in $CO_2$ gas concentration.
9. The average bird weights are then calculated.

The difference between the embodiment of FIGS. 1 and 2 is that in the embodiment of FIG. 2 the control and recording of weights, etc. can be carried out automatically at a remote location. It should be noted that much of the equipment shown internal of the enclosure will in practice be housed within it.

Figure 3:
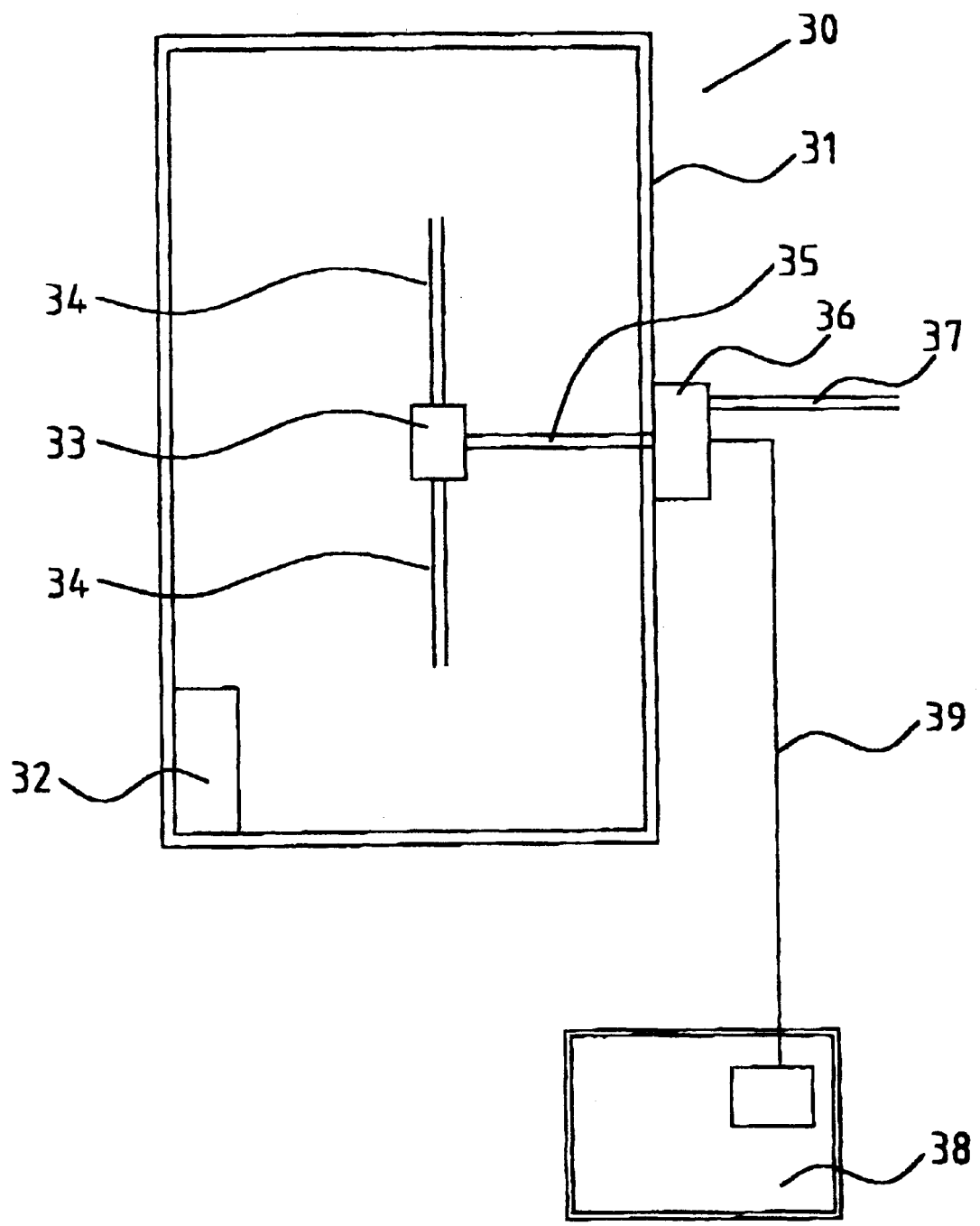
FIG. 3 is a layout of a test unit used.
Figure 4:
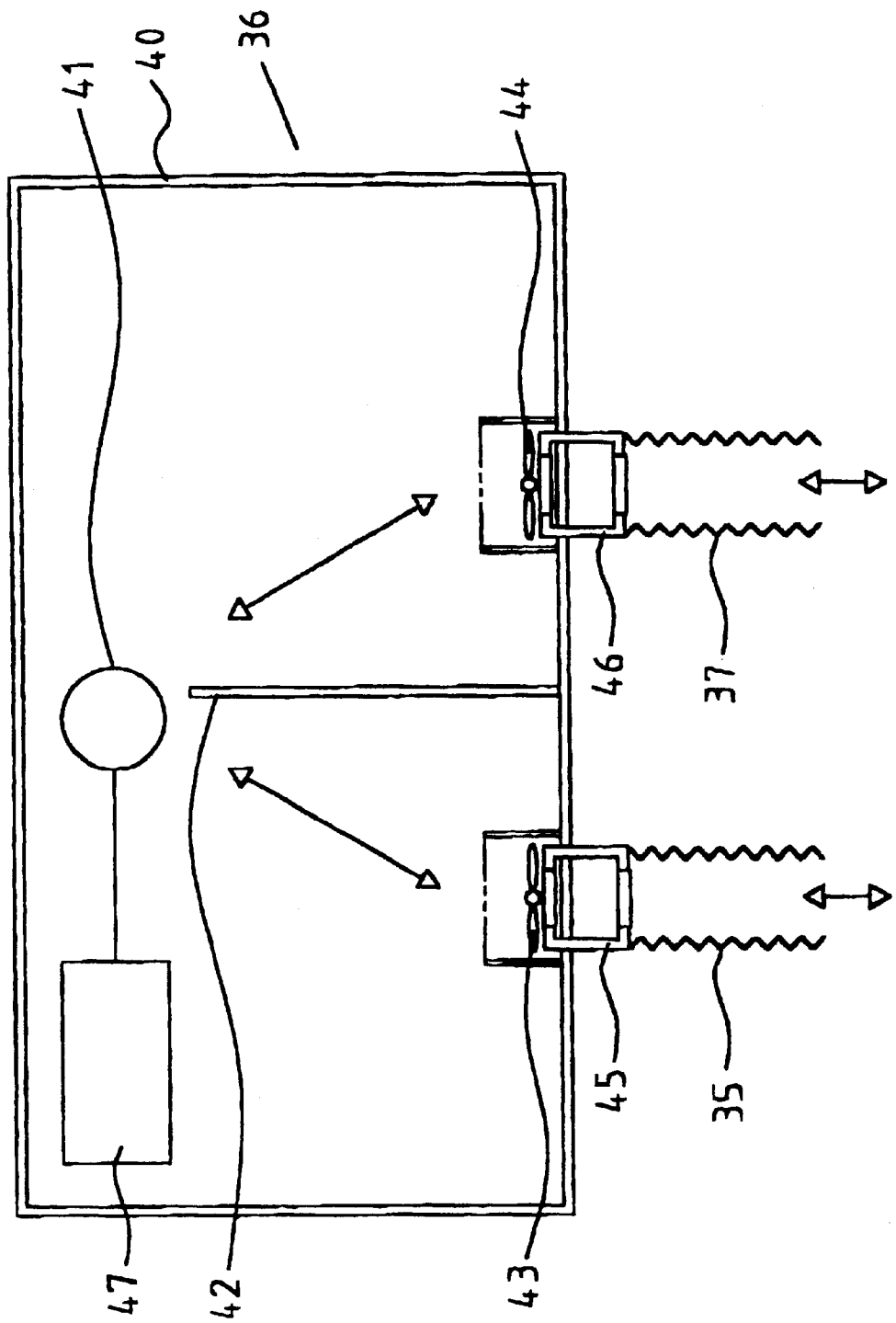
FIG. 4 is a diagrammatic view of a sensor used in the test.

Referring now to FIGS. 3 and 4, there is illustrated a test unit indicated generally by the reference numeral 30 comprising a conventional rearing house 31 having a control room 32 and associated vents, lights and heating (not shown). Mounted in the test unit 30 is a mixer box 33 incorporating baffles (not shown) which connects the mixer box 33 to a pair of air inlet pipes 34. The mixer box 33 is further connected by pipe 35 to a monitoring unit 36 which is connected to an external air inlet pipe 37 and to a central control unit 38. The central control unit 38 is connected to the monitoring unit 36 by a wire 39 but could alternatively be connected via a wireless communication device.

Referring now to FIG. 4, the monitoring unit 36 comprises an enclosed box 40 mounting a plurality of air monitoring sensors 41, in this case, a combined temperature sensing and recording device and a $CO_2$ recording device. The enclosed box 40 further mounts an air baffle 42 and a pair of ambient air and rearing house air fans 43 and 44, which in turn are, connected to an inlet formed by glands 45 and 46 respectively. The gland 45 is connected to the pipe 35 and the gland 46 is connected to the external air inlet pipe 37. Strictly speaking, the glands 45 and 46 are combined inlets and outlets. It will be observed that the actual orientation of the connections in FIG. 4 is not the same as in FIG. 3 as all the pipework is not illustrated in FIG. 3. A data transmitter 47 is connected to the sensor 41 and it will in turn be connected to the central control unit 38 either by wires or wireless as the case may be.

Prior to the test, the tan 44 was run continuously, thus introducing fresh air into the monitoring unit 36 which in turn expels fresh air through the pipe 35 into the rearing house 31. The fresh air therefore ventilated the rearing house 31 and cleaned the pipe 35, mixer box 33 and air inlet pipes 34. At the same time, the sensors 41 were operating thus recording $CO_2$ levels. This allowed continual calibration of the ambient $CO_2$ level in fresh air usually 350 to 400 ppm $CO_2$. During the test and during the operation of a unit, the fan 44 is stopped and the fan 43 operated now drawing air from the rearing house 31 into the monitoring unit 36 to sense the ambient temperature and $CO_2$ concentration in the rearing house 31. In this particular test, it was found that the $CO_2$ concentration at that particular time was of the order of 1000 ppm $CO_2$, that is to say, before a test was carried out.

Figure 5:
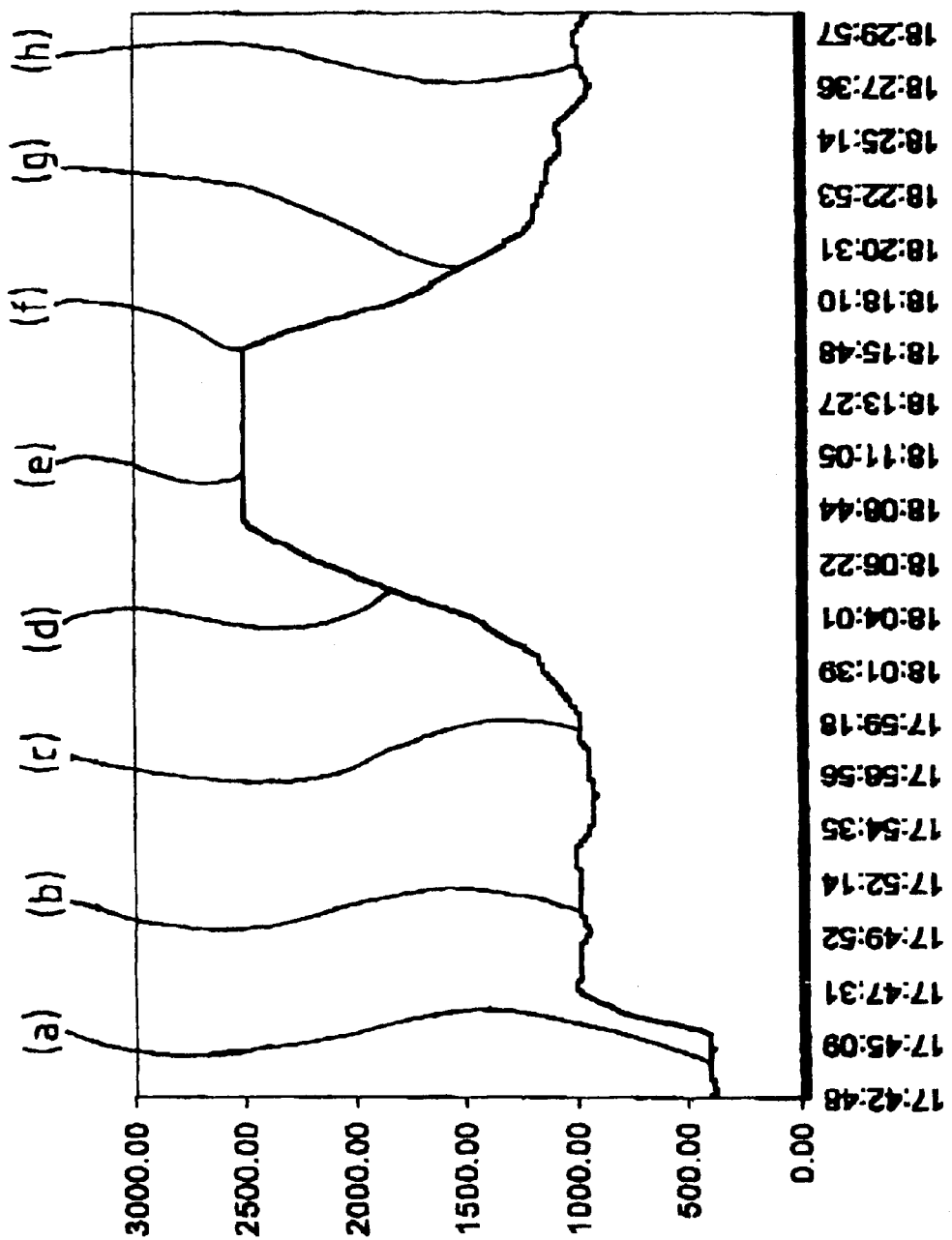
FIG. 5 is a graphical representation of the carbon dioxide concentration in the test unit over the test.
Figure 6:
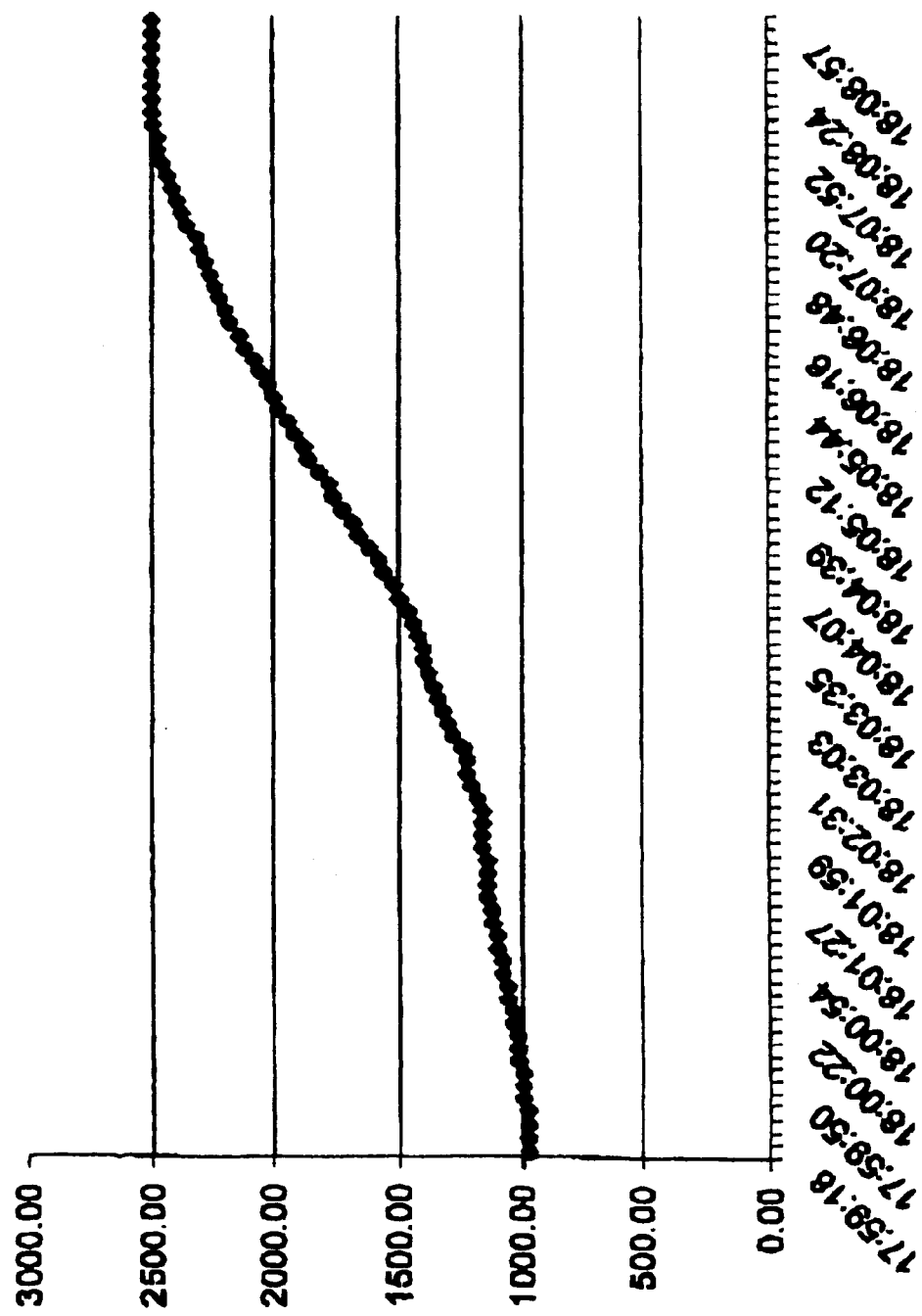
FIG. 6 is a detailed graphical representation of portion of the test results illustrated in FIG. 5.

In the particular test, details of which are oven in FIGS. 5 to 6, the lights were not turned off nor were the birds allowed to settle. All the ventilation was closed and the fan 44 stopped and the fan 43 operated. Thus, only a small amount of air was being excavated from the rearing house 31. It should be noted that the length of time over which the test was carried out was excessive and the birds experienced some discomfort. It would not be normal to carry out the test for such a length of time. It is believed that the sensors saturated. It is expected that while in FIG. 5, the $CO_2$ level is shown as having plateaued out, in fact, it is believed that the $CO_2$ level reached much higher concentrations of the order of 3,500 ppm. This was considered excessive.

Referring now to FIG. 5, at (a) the fan 43 is operating and the ambient air $CO_2$ is being sensed which, it will be seen, is somewhat below 500 ppm. Then the fan 44 is stopped and the tan 43 is operated so that the $CO_2$ concentration within the test unit 30 is sensed at (b). Then at (C), the test commences by cutting oft all the other ventilation to the rearing house 31. Then the $CO_2$ concentration within the teat unit 30 starts to rise as illustrated by the portion of the graph identified by (d). As explained already, in the test, the amount of $CO_2$ sensed leveled out which was due to the $CO_2$ sensor saturating. Accurate measurements of the true $CO_2$ concentration were not obtained, however, extrapolating the curve, it is likely that the $CO_2$ levels in the test reached 3,500 ppm. This was simply allowed to establish operational limits. However, it was felt that in practice, the $CO_2$ level would not be allowed to rise above 2,500 ppm. Then at (1), the ventilators to the rearing house 31 were opened and as can be seen from the portion (g), the $CO_2$ concentration reduced relatively rapidly until the $CO_2$ level leveled out to the position illustrated by the portion identified by (h) which corresponds to the portion (b) previously sensed.

Referring now to FIG. 6, there is illustrated in more detail, the rise of the $CO_2$ concentration over a specific period, that is to say, the portion (d) of FIG. 5. The following table gives the results that can be obtained from FIG. 6.

| Date | Time | $CO_2$ ppm | degC box |
|---|---|---|---|
| 07/08/00 | 18:04:01 | 1500.00 | 23.37 |
| 07/08/00 | 18:05:44 | 2000.00 | 23.45 |

This gives a $CO_2$ rate=(2000−1500)/(1 mm 43 sec)=291 ppm/minute using a beat fit analysis.

It is envisaged that all that will be required is to monitor the time it takes, for example for the $CO_2$ concentration to rise to 2,000 ppm and this will be sufficient to monitor the situation. It is expected that either a fixed level will be set and monitoring will be carried out and the time recorded to reach that particular level of $CO_2$ concentration or alternatively the concentration of $CO_2$ will not be allowed to exceed 2250 ppm. The monitoring can also be carried out over a fixed period of time. This can be done on a daily basis. All the tests to date establish that the rate of use of $CO_2$ gas emission correlates with bird weight in a consistent manner.

Figure 7:
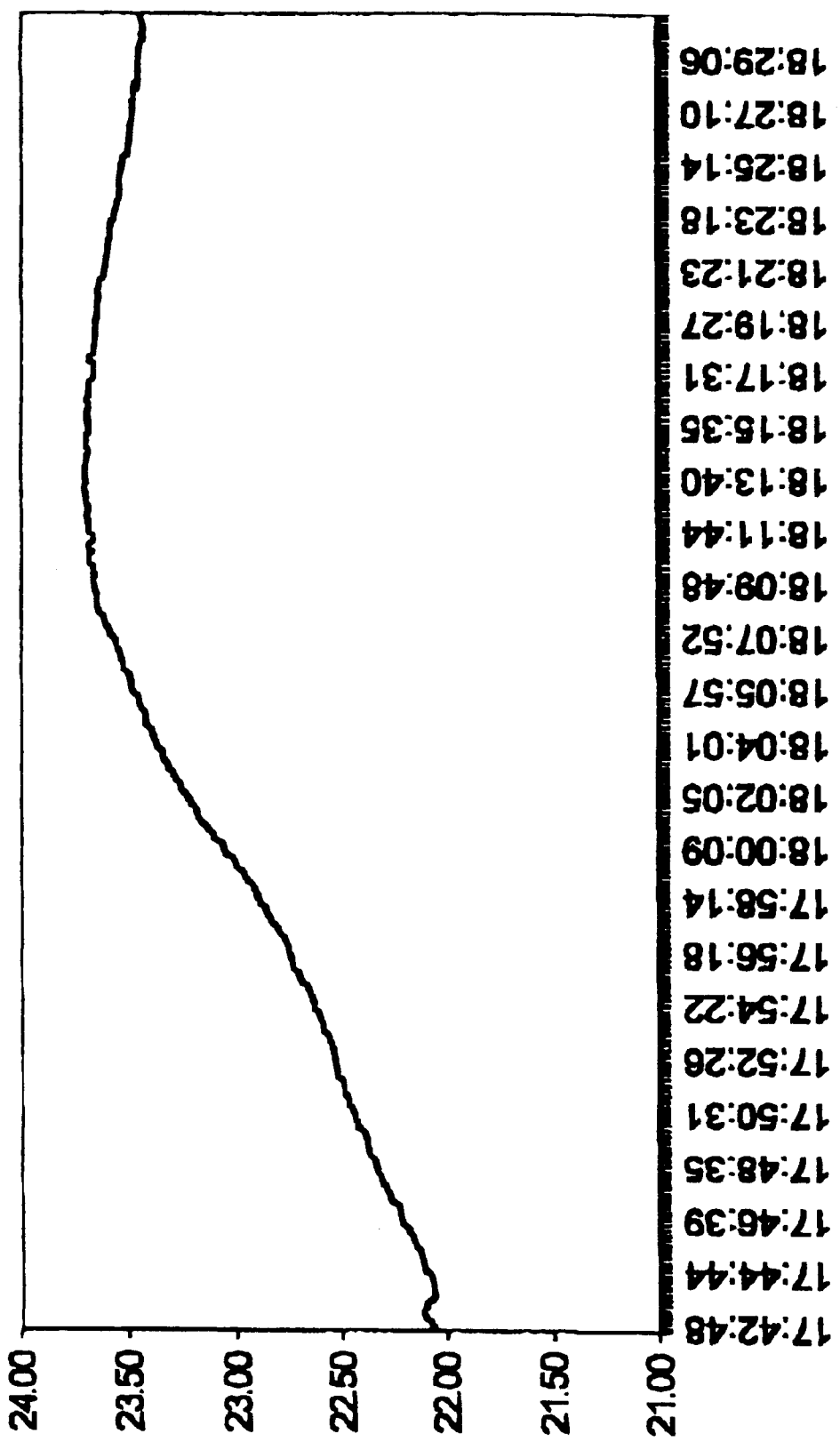
FIG. 7 is a graphical representation of the temperature in the test unit during the test.

It should be noted that FIG. 7 shows how the temperature rose considerably in the rearing house during the test.

It is envisaged that sensors other than carbon dioxide and temperature sensors may be used and that any other gas sensor such as for ammonia may be used as well as humidity and other sensors. Indeed, a full record of the ambient conditions within any rearing house may be obtained.

A particularly suitable carbon dioxide detector is one using the principle of a solid electrolyte formed between two electrodes which is maintained at a specific temperature and the electromotive force (EMF) generated between the two electrodes is measured. This is an extremely sensitive form of $CO_2$ measurement and a typical unit is the TGS 4156 sold by Figaro Inc.

While in all the tests described, the ventilation to the rearing house has been cut off fully, it will be appreciated that this may not necessarily be required, nor indeed may it be necessary to cut off the ventilation at all. It will be appreciated that with the same ventilation, it will be possible to measure the increase in $CO_2$ concentration in a rearing house over a longer period of time such as 24 hours. Further, it will be possible to partially cut off the ventilation to carry out the test. Indeed, the variations in the test conditions are many.

Further, it is envisaged that a crop rearing house manufactured in accordance with the invention in which there is a gas sensor for determining the concentration of selected gases in the environment will be particularly suitable for rearing. The advantage will be that if continuous monitoring is carried out, then sudden spikes in metabolic activity or, for example, increases in water usage, will alert the operator to the possibility of disease or other problems. Also, the $CO_2$ detection can be used to activate alarms for a faster response to difficulties within the rearing house. At the present moment, the only detection carried out is that at temperature and by the time the excessive temperature has been reached, considerable damage may have been done to the animals. Thus, the present invention as well as assisting in the more accurate control of the rearing of the animals in the sense of monitoring body weight and development generally, will also assist in the monitoring of other animal and plant conditions which can be commercially very useful.

It will be appreciated that these calculations cannot be carried out until sufficient controlled experimental calculations have been carried out to allow the total bird weight to be calculated. The easiest way of doing this initially is to simply carry out the normal bird weight estimations and to release the birds for subsequent processing in accordance with normal practice. However, immediately prior to releasing the birds the above test is carried out so that the increase in $CO_2$ gas concentration can be calculated. After a sufficient number of tests have been carried out a suitable calibration can be achieved.

It needs to be emphasised that as well as sensing $CO_2$, equally well oxygen could be sensed which would have the same effect. It is preferable that when the concentration, for example, of $CO_2$ exceeds a preset limit, the test is stopped and the change in concentration of the $CO_2$ or the other control gas is measured.

Ideally, some form of look up database will be provided in which the various development assessments of a crop or the weight, for example, of animals, can be entered and then that database can be used for future estimation.

It will be appreciated that additionally, the gas constituents in the air being removed from the enclosure can be measured at other times to enable the control of the air input for optimal environmental conditions. As well as measuring the weight of, for example, an animal, the invention also provides a method of rearing a crop using this method of measuring the weight of the crop and what would normally be done is to divide the expected crop rearing time into a number at control periods. Then, the body weight of the crop of animals can be determined at the end of each control period and then it will be possible for the crop owner or supervisor to very the growing conditions for the next control period to take account of the previously recorded weight to obtain a desired weight again for the next control period. It will be appreciated that in many instances for example, when rearing poultry or pigs, the time at which the pigs should be ready for harvesting can vary depending on customers requirements. Thus, for example, the rearer or operator might wish not to achieve the optimum weight for a longer period than originally expected or maybe might wish to achieve the optimum weight quicker than required and thus the present invention allows such variation in the growing conditions to be achieved. Further, with the present invention, it will be possible to vary the environmental conditions and the food quantities and type to obtain tests of various desired weight gains. This will be carried out by performing a number of tests on separate samples of crop for each control period. Thus, a database of the rearing conditions and weight gains for each control period can be provided to give the operator the optimum growing conditions for a specific control period having regard to initial crop weight at the start of the control period and desired crop rate at the end of the period.

It should be noted that this system is relatively accurate in that a standard number of birds are generally supplied from a hatchery per crop. The mortality of the birds is recorded in accordance with standard practice and thus the total number of birds at any one time in the hatchery is known. Further bird genetics are uniform and more importantly, birds are the only significant source of $CO_2$ gas at lime of measurement.

While in this specification considerable emphasis is placed on animal weight which is closely related to the metabolic activity of the animal, for plants the size and slate of development may be reflected by $CO_2$ generation. Thus weight is in a sense only applicable to animals.

The present invention has considerable advantages over what is used at present in that in effect a fully accurate average weight of the birds is achieved while at the same time all the control equipment is already installed. This usually includes as mentioned above computers and the like for the control of the ventilation equipment thus all that is required is to reprogram the computer control equipment somewhat to report the information and to connect a gas detector to it.

It will also be appreciated that the measurement of $CO_2$ gas can be used to actually determine the optimum ventilation requirements within the enclosure. This will reduce heating costs and electrical consumption of air exchange fans. Thus it is envisaged that throughout the growing cycle that the $CO_2$ gas concentration can be measured.

It will be noted that the same affect would be achieved just as easily by measuring the rate in decline of oxygen gas in the enclosure over a pre-set time.

While the example described above has been described with respect to animals, namely, chickens it will be appreciated that the method could be useful for other types of intensive production such as the production of pigs, cattle for veal and so on.

Similarly the method according to the invention may be used for other horticultural and agricultural use such as the intensive growing of mushrooms and other crops.

In the specification the terms "comprise comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail within the scope of the claims.

What is claimed is:

1. A method of determining development of a crop housed with a plurality of similar crops in an enclosure having means to provide a controlled environment comprising:

analysing the gas constituents of the ambient air at a start of a test period;

analysing the gas constituents of the ambient air at the end of the test period;

obtaining the rate of change in concentration of at least one control gas in the ambient air during the test period which rate of change in concentration of the control gas is a measure of the metabolic activity rate of the crop housed in the enclosure;

controlling a duration of the test period by measurement of a concentration of oxygen within the enclosure;

obtaining an estimate of the metabolic activity of the crop; and obtaining an estimate of the development of the crop from the metabolic activity of the crop.

2. A method as claimed in claim 1, in which the increase in the quantity of carbon dioxide in the environment is determined.

3. A method as claimed in claim 1, in which the decline in the quantity of oxygen is measured.

4. A method as claimed in claim 1 in which:
the crop within the enclosure is caused to assume a rest phase with minimal activity;
a period of time is allowed to pass with the crop in the rest phase;
the enclosure is sealed; and
the test is carried out.

5. A method as claimed in claim 1, in which the additional act is performed of sealing the enclosure during the test period.

6. A method as claimed in claim 1, in which the step is performed of causing the air to be recirculated within the enclosure during the test period.

7. A method as claimed in claim 1, in which:
the enclosure is sealed dunng the test period to prevent the ambient air being changed;
carbon dioxide is chosen as the control gas and the change in the concentration of carbon dioxide is measured during the test period; and
when the concentration of carbon dioxide exceeds a preset limit, the test is stopped and the change in concentration of the carbon dioxide is measured as the control gas measurement.

8. A method as claimed in claim 1, in which the metabolic rate of the crop is compared to the actual development to calibrate the measurement.

9. A method as claimed in claim 1 comprising:
assessing the actual development of all the crop,
providing an average development assessment of the crop for each individual crop element,
storing the development assessment and the rate of change of the control gas in a look-up database, and
repeating the tests on the crop to provide further data for the database.

10. A method as claimed in claim 1, in which additionally the gas constituents in the air being removed from the enclosure are measured to enable the control of the air input for optimal environmental conditions.

11. A method of determining development of a crop housed with a plurality of similar crops in an enclosure having means to provide a controlled environment comprising:
analysing the gas constituents of the ambient air at a start of a test period;
analysing the gas constituents of the ambient air at the end of the test period;
obtaining the rate of change in concentration of at least one control gas in the ambient air during the test period which rate of change in concentration of the control gas is a measure of the metabolic activity rate of the crop housed in the enclosure;
obtaining an estimate of the metabolic activity of the crop;
obtaining an estimate of the development of the crop from the metabolic activity of the crop;
causing the crop within the enclosure to assume a rest phase with minimal activity;
allowing a period of time to pass with the crop in the rest phase;
sealing the enclosure; and
carrying out the test.

* * * * *